(12) United States Patent
Robert

(10) Patent No.: US 11,077,127 B2
(45) Date of Patent: Aug. 3, 2021

(54) **ADJUVANT CONTAINING BAICALIN, PARTICULARLY FROM A *SCUTELLARIA BAICALENSIS* EXTRACT, AND ANIMAL FEED CONTAINING SUCH AN ADJUVANT**

(71) Applicant: DELTAVIT, Janze (FR)

(72) Inventor: Fabrice Robert, Guichen (FR)

(73) Assignee: DELTAVIT, Janze (FR)

( * ) Notice: Subject to any disclaimer, the term of this patent is extended or adjusted under 35 U.S.C. 154(b) by 0 days.

(21) Appl. No.: 16/553,218

(22) Filed: Aug. 28, 2019

(65) Prior Publication Data

US 2019/0381083 A1 Dec. 19, 2019

Related U.S. Application Data

(62) Division of application No. 14/910,707, filed as application No. PCT/FR2015/050450 on Feb. 25, 2015, now abandoned.

(30) Foreign Application Priority Data

Feb. 25, 2014 (FR) ...................................... 1451501

(51) Int. Cl.

| | | |
|---|---|---|
| *A61K 31/7048* | (2006.01) | |
| *A61K 36/539* | (2006.01) | |
| *A23K 50/75* | (2016.01) | |
| *A23K 50/30* | (2016.01) | |
| *A61K 31/00* | (2006.01) | |
| *A23K 20/00* | (2016.01) | |
| *A23K 20/10* | (2016.01) | |
| *A23K 50/80* | (2016.01) | |
| *A61K 31/352* | (2006.01) | |
| *A23K 50/10* | (2016.01) | |
| *A23K 20/121* | (2016.01) | |

(52) U.S. Cl.
CPC .......... *A61K 31/7048* (2013.01); *A23K 20/00* (2016.05); *A23K 20/10* (2016.05); *A23K 20/121* (2016.05); *A23K 50/10* (2016.05); *A23K 50/30* (2016.05); *A23K 50/75* (2016.05); *A23K 50/80* (2016.05); *A61K 31/00* (2013.01); *A61K 31/352* (2013.01); *A61K 36/539* (2013.01)

(58) Field of Classification Search
CPC ..... A61K 31/7048; A23K 50/10; A23K 50/30
See application file for complete search history.

(56) References Cited

U.S. PATENT DOCUMENTS

2010/0233756 A1* 9/2010 Sunvoid ................ A23K 50/40
435/34

FOREIGN PATENT DOCUMENTS

| CN | 101167529 A | 4/2008 |
|---|---|---|
| CN | 101491295 A | 7/2009 |
| CN | 101816382 A | 9/2010 |
| CN | 101971933 A | 2/2011 |
| CN | 102599380 A | 7/2012 |
| CN | 102805271 A | 12/2012 |
| CN | 102934757 A | 2/2013 |
| CN | 103315145 A | 9/2013 |

OTHER PUBLICATIONS

Chou T.-C., Chang, L.P., Li, C.-Y., Wong, C.-S., & Yang, S.-P. (2003). The Anti-inflammatory and Analgesic Effects of Baicalin in Carrageenan-Evoked Thermal Hyperalagesia. Anesthesia & Analgesia, 2003, 1724-1729, doi:10.1213/01.ANE.0000087066.71572.3F.

Rice-Evans, C. A., Miller, N. J., & Paganga, G. (1996). Structure-antioxidant activity relationships of flavonoids and phenolic acids. Free Radical Biology and Medicine, vol. 20, No. 7, pp. 933-956.

Trevisi, E., Zecconi, A., Bertoni, G., & Piccinini, R. (2010). Blood and milk immune and inflammatory profiles in periparturient dairy cows showing a different liver activity index. The Journal of Dairy Research, vol. 77(3), pp. 310-317. doi:10.1017/S0022029910000178.

Ballou, M.A., Immune Responses of Holstein and Jersey Calves During the Pre Weaning and Immediate Post-Weaning Periods When Fed Varying Planes of Milk Replacer, Journal of Dairy Science, 2012; 95(12): 7319-30.

Chou, T.-C., Chang, L.-P., Li, C.-Y., Wong, C.-S., & Yang, S.-P. (2003). The Anti-inflammatory and Analgesic Effects of Baicalin in Carrageenan-Evoked Thermal Hyperalagesia.

Farney, J.K., Mamedova, L.K., Coetzee, J.F., Minton, J.E., Hollis, L.C., Bradford, B.J., Sodium salicylate treatment in early lactation increases whole-lactation milk and milk fat yield in mature dairy cows, Journal of Dairy Science, 2013;96(12):7709-18.

Hsieh, C.-J., Hall, K., Ha, T., Li, C., Krishnaswamy, G., & Chi, D. S. (2007). Baicalein inhibits IL-Ibeta- and TNF-alpha-induced inflammatory cytokine production from human mast cells via regulation of the NF-kappaB pathway. Clinical and Molecular Allergy : CMA, 5, 5. doi:10.1186/1476-7961-5-5.

Kim, H. P., Son, Km H., Chang, H. W., & Kang S. S. (2004). Critical Review Anti-inflammatory Plant Flavonoids and Cellular Action Mechanisms. Journal of Pharmacological Sciences, 245, 229-245.

Klasing, K. C., Korver D. R., & Korver I. (1997). Leukocytic Cytokines Regulate Growth Rate and Composition Following Activation of the Immune System 1. Journal of Animal Science, 75, 58-67.

Niewold T. a. (2007). The nonantibiotic anti-inflammatory effect of antimicrobial growth promoters, the real mode of action? A hypothesis. Poultry science, 86(4), 605-9.

Sordillo, L.M., Raphael, W., Significance of Metabolic Stress, Lipid Mobilization, and Inflammation on Transition Cow Disorders, Vet Clin North Am Food Anim Pract, 2013;29(2):267¬78.

(Continued)

*Primary Examiner* — Pancham Bakshi

(74) *Attorney, Agent, or Firm* — Arrigo, Lee, Guttman & Mouta-Bellum LLP

(57) ABSTRACT

The invention relates to a nutritional adjuvant, comprising baicalin and/or baicalein diluted on a medium, and to a feed comprising such an adjuvant, for improving production performance in farm animals in stressful situations.

4 Claims, 3 Drawing Sheets

(56) References Cited

OTHER PUBLICATIONS

Figure 1:
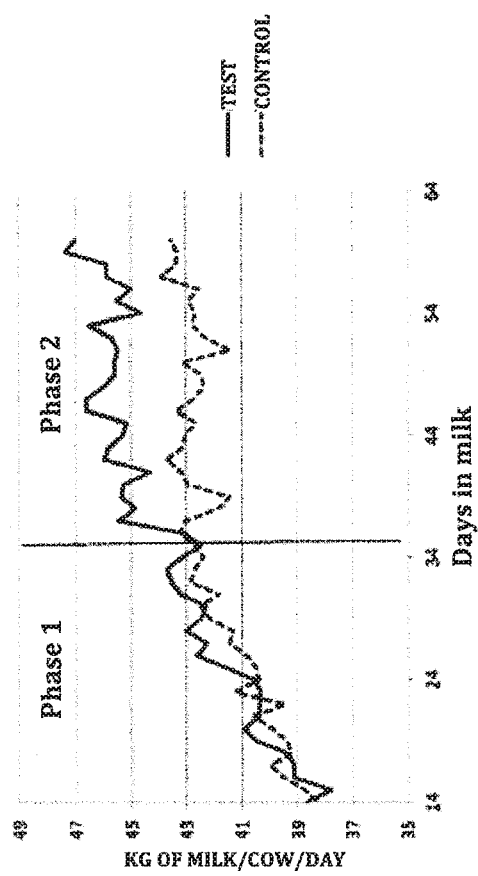

International Search Report for Application No. PCT/FR2015/050450 dated Jun. 3, 2015.
Machine English translation CN 101491295A; translated May 7, 2019.
Arcuri (how to make your own chicken feed; https://www.thespruce.com/make-chicken-or-poultry-feed-3016558; Apr. 2019).
Chou (Anesthesia & Analgesia, 2003, 1724-1729).

* cited by examiner

ADJUVANT CONTAINING BAICALIN, PARTICULARLY FROM A *SCUTELLARIA BAICALENSIS* EXTRACT, AND ANIMAL FEED CONTAINING SUCH AN ADJUVANT

FIELD OF THE INVENTION

The technical field of the present invention involves feed additives and feed for farmed animals. More specifically, the present invention involves plant extracts to maintain and increase the productivity in productive farmed animals in uncomfortable conditions.

Uncomfortable conditions generate stress and are correlated with physiological and behavioural changes that render farmed animals sensitive to disease. These stressful conditions have an even more negative impact on their wellbeing. One of the consequences is a reduction in the productivity of these weakened animals, whether it be milk production, eggs, meat or any other product. The phases of discomfort and stress are also characterised by a production below the genetic potential of the animals.

Performance improvements have been used and incorporated in the feed, in particular antibiotics intended, in ruminants for example, to orient the rumen fermentation by only selecting the beneficial bacteria.

These antibiotic improvements also stimulate the production of farmed animals by reducing inflammation (Niewold, 2007). Indeed, inflammatory phenomena reduce the production of meat, milk and eggs (Klasing et al, 1997; Trevisi et al, 2010) situations of discomfort or stress such as birthing, weaning, thermal or environmental changes, non-adapted conditions, etc.

Moreover, the use of antibiotics by farmers follows the occurrence of situations of discomfort or stress.

These antibiotic improvements represent potential public health risks by the development of resistances in bacteria and rejection by some consumers.

A great many plant extracts demonstrate anti-inflammatory and anti-oxidant effects (Kim et al, 2004; Rice-Evans et al, 1996). They represent natural nutritional alternatives able to act simultaneously on the wellbeing of farmed animals and the maintenance of their production, whatever the farming conditions. These plant extracts may be incorporated in animal feed, food supplements or in their drinking water.

STATE OF THE TECHNIQUE

Patent application CN102805271 discloses an anti-stress, anti-diarrhoeal, pro-growth feed additive for weaned piglets derived from Chinese herbal medicine. This additive is obtained by a mixture of finely ground *Astragalus mongholicus, Scutellaria baicalensis*, malt, liquorish, dang shen, *Poria cocos* and the rhizome of Atractylode. According to Chinese herbal medicine, the additive in the present invention may increase the growth performance of weaned piglets, the additive has anti-diarrhoeal effects; the development of the gastro-intestinal tract of weaned piglets may be improved; the activity of the digestive enzymes of the gastro-intestinal tract may be improved to support the development of the digestive enzyme system of pigs; the micro-ecological environment of the digestive tract of pigs may be regulated and stabilised to accelerate the growth of the pigs; the anti-oxidant function of the organism of weaned piglets may be improved to reinforce the compensating capacities of the pigs when confronted with environmental irradiation; the shape of the intestinal mucosa is improved to avoid the collapse of the intestinal villi and reinforce the restoration of the intestinal tract; and the immunological function of the intestinal mucosa in weaned piglets may be regulated.

Patent application CN103315145 presents a feed for weaned piglets comprising an additive consisting of Chinese yam, purple perilla, *Scutellaria baicalensis*, dafflower, *Houttuynia cordata*, Leonurus, Radix dichroa and liquorice. The feed for piglets may provide basic nutritive substances once the piglets have been weaned. At the same time, the growth and immunity of the piglets may be increased by the addition of the additive.

Patent application CN101816382 describes a feed additive and its use in the resistance to disease and to increase egg-laying. This additive includes a mixture of plant extracts known in traditional Chinese medicine including a *Scutellaria baicalensis* extract.

Patent application CN101971933 describes a prenatal nutritional additive and a post-partum nutritional additive comprising a mixture of different plants from traditional Chinese medicine such as *Scutellaria*. These two additives are administered to cows before and after calving. These perinatal additives help improve the post-partum immunity, their health and their milk production.

*Scutellaria baicalensis* is an Asian plant. Its extracts in particular include two active ingredients from the flavonoids, baicalin and baicalein. The latter demonstrate an anti-inflammatory action (Chou et al, 2003; Hsieh et al, 2007) and an anti-viral action.

Non-Patented Literature Mentioned:

Ballou, M. A., Immune responses of Holstein and Jersey calves during the pre-weaning and immediate post-weaning periods when fed varying planes of milk replacer, *J. Dairy Sci*, 2012; 95(12):7319-30

Chou, T.-C., Chang, L.-P., Li, C.-Y., Wong, C.-S., & Yang, S.-P. (2003). The Anti-inflammatory and Analgesic Effects of Baicalin in Carrageenan-Evoked Thermal Hyperalagesia. *Anesthesia & Analgesia*, 1724-1729. doi:10.1213/01.ANE.0000087066.71572.3F Farney, J. K., Mamedova, L. K., Coetzee, J. F., Minton, J. E., Hollis, L. C., Bradford, B. J., Sodium salicylate treatment in early lactation increases whole-lactation milk and milk fat yield in mature dairy cows, *J. Dairy Sci*, 2013; 96(12):7709-18

Hsieh, C.-J., Hall, K., Ha, T., Li, C., Krishnaswamy, G., & Chi, D. S. (2007). Baicalein inhibits IL-1beta- and TNF-alpha-induced inflammatory cytokine production from human mast cells via regulation of the NF-kappaB pathway. *Clinical and molecular allergy: CMA*, 5, 5. doi:10.1186/1476-7961-5-5

Kim, H. P., Son, K. H., Chang, H. W., & Kang, S. S. (2004). Critical Review Anti-inflammatory Plant Flavonoids and Cellular Action Mechanisms. *Journal of Pharmacological Sciences*, 245, 229-245.

Klasing, K. C., Korver, D. R., & Korver, I. (1997). Leukocytic Cytokines Regulate Growth Rate and Composition Following Activation of the Immune System 1. *Journal of Animal Science*, 75, 58-67.

Niewold, T. a. (2007). The nonantibiotic anti-inflammatory effect of antimicrobial growth promoters, the real mode of action? A hypothesis. *Poultry science*, 86(4), 605-9.

Rice-Evans, C. A., Miller, N. J., & Paganga, G. (1996). Structure-antioxidant activity relationships of flavonoids and phenolic acids. *Free radical biology and medicine*, 20(7), 933956.

Sordillo, L. M., Raphael, W., Significance of metabolic stress, lipid mobilization, and inflammation on transition cow disorders, *Vet Clin North Am Food Anim Pract*, 2013; 29(2):26778

Trevisi, E., Zecconi, A., Bertoni, G., & Piccinini, R. (2010). Blood and milk immune and inflammatory profiles in periparturient dairy cows showing a different liver activity index. *The Journal of dairy research*, 77(3), 310-7. doi:10.1017/S0022029910000178

DISADVANTAGES OF THE PRIOR ART

The solutions in the prior art consist of complex associations of different plant extracts requiring fine dosages. These associations and their dosages are intended for a specific species at a given stage of development, for example, just weaned piglets.

The solutions in the prior art aren't immediately applicable for all productive farmed animals.

In addition, these solutions consist of raw plant extracts. However, the active ingredients in the composition of the extracts vary and, in these conditions, it isn't possible to ensure the invariability of the effects. This variability may even induce an inefficacy. The variability according to the different preparations of extracts and the mixture of extracts is very high and raises concern as to the reproducibility and reliability. In addition, since the mixtures in the prior art are highly complex, it isn't possible to determine the effect of a given extract. However, to ensure a constant effect, it's necessary to have identified the extract responsible for the searched for biological activity, be able to dose one or several active ingredients characterising the extract and the associated effects and ensure a constant intake in the animals, corresponding to the active dose.

SOLUTION PROVIDED BY THE INVENTION

The present invention proposes, as understood in its broadest sense, to correct the disadvantages of the prior art by proposing a nutritional adjuvant to improve the production performance by farmed animals in a stressful situation, consisting of baicalin and/or baicalein diluted on a vehicle. The invention may also comprise baicalin and baicalein derivatives.

Advantageously, baicalin and/or baicalein are provided by a *Scutellaria baicalensis* extract.

Surprisingly, the applicant observed that extracts, in particular the root of *Scutellaria baicalensis*, incorporated in the feed of productive farmed animals increased their production and normalised the disorders caused by stressful situations without having to resort to any type of medication, in particular antibiotics. The *Scutellaria baicalensis* root extract, specifically comprises the active ingredients of baicalin and baicalein. These molecules can be traced throughout the production of adjuvants and feed in accordance with the invention. This enables a very fine control of the dose administered and ingested by the animal in its diet.

According to another method, baicalin and/or baicalein are obtained by chemical synthesis.

Baicalin and/or baicalein may be obtained by extraction or chemical synthesis according to the methods known to the person skilled in the art.

Preferentially, the adjuvant comprises baicalin and baicalein although it may only include one of the two molecules. Preferentially, baicalin and or baicalein are derived from a *Scutellaria baicalensis* root extract.

The *Scutellaria baicalensis* extract is preferentially an extract from the root of the plant, in powder form and obtained by hydro-alcohol extraction. The *Scutellaria baicalensis* extract may be in dry or liquid form. The extract comprises a known quantity in weight of the active ingredient consisting of baicalin and or baicalein, classically between 10 and 50% in weight of baicalin.

This nutritional adjuvant may be used in all productive farmed animals, such as and without limitation, poultry, rabbits, ruminants, sheep, cattle, goats, horses, fish, crustaceans and pigs. Productive farmed animals refers to animals kept for the production of foodstuffs. The adjuvant according to the invention is well tolerated by all productive farmed animals and the safety is good in these species.

The nutritional adjuvant consists of baicalin and/or baicalein diluted on a vehicle. The baicalin and/or baicalein is distributed to the animal at a dose ranging from 0.1 to 20 mg per kg of live weight and per day.

Preferentially, the dose of baicalin and/or baicalein ranges from 0.1 to 10 mg/kg of live weight and per day, more preferentially between 0.1 and 5 mg/kg, and even more preferentially between 0.1 and 2 mg/kg of live weight and per day.

The adjuvant is obtained by dilution of the dry extract of *Scutellaria baicalensis* on a vehicle, the aforementioned vehicle may be liquid if it is intended for a drink or the aforementioned vehicle may be solid if intended for a solid feed product. If the final destination is to be mixed with the drinking water of productive farmed animals, then the dilution vehicle may be water or a mixture of water and mineral salts and/or trace elements or any other additive or solvent known to the person skilled in the art as being classically incorporated in drinking water. If the final destination is a solid feed, the vehicle may comprise a grain or a mixture of grains such as wheat, barley, oats or any other raw material or additives, solvents, mineral salts and/or trace elements known to the person skilled in the art.

A situation of discomfort or stress is understood as all of the environmental conditions having a negative impact on the production of productive farmed animals. It involves stimuli well known to the person skilled in the art having an impact on the physiology and behaviour of the animals, by no means limited to variations in temperature, humidity, light, the proximity of other animals, birthing, weaning, transport, contact with humans, changes in the environment, etc.

The nutritional adjuvant according to the invention stimulates the feed conversion and/or feed consumption of animals in a situation of discomfort and/or stress.

Feed conversion refers to the ratio between the dry weight of the feed distributed and the increase in production obtained. The nutritional adjuvant according to the invention is understood to increase the productivity of productive farmed animals by increasing the feed conversion, that is, at an equal weight of a given feed, the growth of the animal is higher and the productivity is better.

Feed consumption refers to the daily ration consumed by each animal. The nutritional adjuvant according to the invention is understood to stimulate the appetite of the animals and as a result, their production.

Advantageously, the nutritional adjuvant is applied to the stimulation of lactation in animals in a situation of discomfort, the stimulation of the production of eggs in animals in a situation of discomfort, the stimulation of growth of animals in a situation of discomfort, the stimulation of the resistance to disease in animals in a situation of discomfort.

The nutritional adjuvant according to the invention does not comprise antibiotics.

The invention also comprises a feed for animals comprising a nutritional adjuvant intended to improve the production performance by animals in a situation of discomfort or stress, comprising an extract of *Scutellaria baicalensis*, of known concentration in flavonoid, or synthetic flavonoid active ingredients, the aforementioned flavonoids preferentially being baicalin and/or baicalein as well as their derivatives.

The feed may come in the form of a liquid, pulp, paste, granules, powders or any other solid form. It comprises the adjuvant on a vehicle, comprising baicalin and/or baicalein flavonids, preferentially, a extract of *Scutellaria baicalensis*, providing the animals with between 0.1 and 20 mg/kg of live weight and per day of baicalin/baicalein active ingredient.

The feed comprising an adjuvant according to the invention may be used in the improvement of production performance by animals in a situation of discomfort, in the stimulation of lactation in animals in a situation of discomfort, in the stimulation of the production of eggs in animals in a situation of discomfort, in the stimulation of growth in animals in a situation of discomfort or even in the stimulation of the resistance to disease in animals in a situation of discomfort.

DESCRIPTION

To demonstrate the efficacy of the adjuvant according to the invention, in vivo tests were carried out in different productive farmed animals species subject to a stress.

FIG. 1 presents the results in the evolution in the average daily milk production in the cow receiving feed in accordance with the invention.

Figure 2:
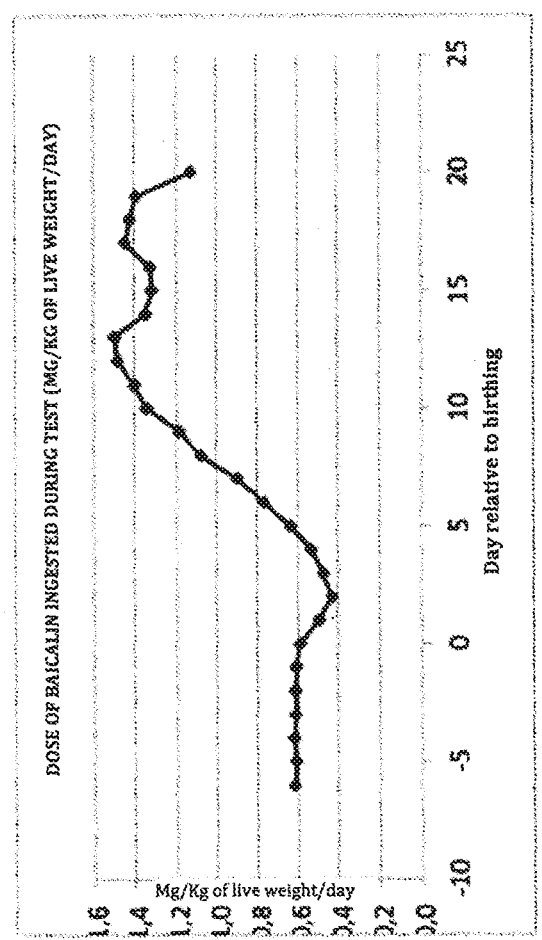

FIG. 2 presents the dose of baicalin ingested by sows during test 2.

Figure 3:
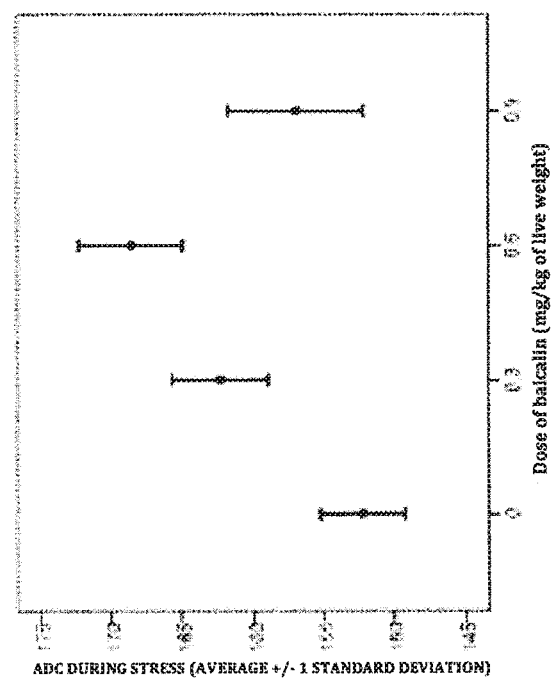

FIG. 3 presents the effect of the daily dose of baicalin on the feed consumption during the phase of thermal discomfort during test 4.

The situations of discomfort induced by birthing have been shown to be susceptible of altering the state of health and lactation (Ballou, 2012; Farney et al., 2013; Sordillo & Raphael, 2013).

Test 1: Study of the Effect of the Administration of a Feed Comprising the Adjuvant Comprising an Extract of *Scutellaria baicalensis* on a Solid Vehicle on the Milk Production by Dairy Cows Subject to a Stress Protocol:

The test was carried out on a herd of one hundred Prim'Holstein dairy cows.

24 dairy cows calving during the same period were divided into two groups of twelve according to the date of calving, the lactation rank, the amount of milk produced, the fat level, the protein level at day 305 after the previous lactation for the multiparous cows, the milk index for the primiparous cows.

The maize silage ration was identical in both groups except for the addition of an adjuvant according to the invention including 10% of a *Scutellaria baicalensis* extract on a calcium carbonate vehicle. This adjuvant was incorporated at the rate of 0.5% in the production feed (17% raw protein, 1 UFL) distributed at the rate of 2 kg per cow and per day in the test group. Each cow therefore received 1 gram per jour of *Scutellaria baicalensis* extract, that is, 333 mg of baicalin, or 0.5 mg/kg live weight.

Results on the Milk Production:

The milk production was significantly improved over the two months of monitoring. The effect of the *Scutellaria baicalensis* extract on lactation is observed after the first month (phase 2 in FIG. 1). FIG. 1 shows the improvement in the average daily milk production in cows receiving feed supplemented with a *Scutellaria baicalensis* extract in accordance with the invention as compared with the cows in the control group. Table 1 sums up the averages of milk production of the cows according to their feed. The milk production is significantly higher in the group of cows receiving feed supplemented with *Scutellaria baicalensis*.

TABLE 1

Milk production in kg/cow/day

| Group | Total | Period 1 | Period 2 |
|---|---|---|---|
| Scutellaria | 44 | 42.8 | 45.9 |
| Control | 42.5 | 41.7 | 42.9 |
| p | <0.05 | ns | <0.05 |

(ns: non significant)

Test 2: Study of the Effect of a Lactation Feed Comprising a *Scutellaria baicalensis* Extract on the Lactation of Sows.

As opposed to dairy cows where the milk production can be directly measured, the milk production of sows is indirect and is measured by the weight increase in piglets nursed by their mothers (ADWG—Average Daily Weight Gain in grams).

Protocol:

55 sows were divided into two groups. The feed (the characteristics are provided in table 2) was distributed during the entire period of lactation of the sows. The *Scutellaria baicalensis* adjuvant consists of a *Scutellaria baicalensis* extract incorporated at the rate of 1.5% on a vehicle. The TEST feed contained 150 mg of *Scutellaria baicalensis* extract per kg, that is 50 mg of baicalin per kg of feed. The feed was distributed to the sows, three days before birthing until the weaning of the piglets (21 days after birthing). 632 piglets were included in the test.

TABLE 2

Characteristics of the feed distributed to the sows

| | Lactation feed | Control | Test |
|---|---|---|---|
| SOWS | ENT (MJ/kg) | 9.7 | 9.7 |
| | Fatty matter (%) | 5.3 | 5.3 |
| | Raw protein (%) | 16.5 | 16.5 |
| | Raw cellulose (%) | 6.3 | 6.3 |
| | Digestible lysine (%) | 0.9 | 0.9 |
| | Digestible phosphorus (%) | 0.32 | 0.32 |
| | Electrolytic balance$_{(mEq/kg)}$ | 175 | 175 |
| | Digestible Ca/P | 2.8 | 2.8 |
| | Wheat (%)* | 20.0 | 19.0 |
| | Barley (%) | 17.6 | 17.6 |
| | Maize (%) | 8.6 | 8.6 |
| | Milurex (%) | 10.0 | 10.0 |
| | Peas (%) | 6.0 | 6.0 |
| | Soy grain (%) | 3.0 | 3.0 |
| | Soy meal (%) | 7.5 | 7.5 |
| | Canola meal (%) | 4.2 | 4.2 |
| | Sunflower meal (%) | 8.0 | 8.0 |
| | Beet pulp (%) | 6.0 | 6.0 |
| | Canola oil (%) | 2.3 | 2.3 |
| | *Scutellaria Baicalensis* adjuvant* | — | 1.0 |

(*)1% wheat is provided by the adjuvant vehicle.

The feed intake of each sow was recorded and used to calculate the daily dose ingested per kg of live weight and per day during the trial. This daily dose is provided in FIG. 2.

Results of Test 2:

The TEST feed does not differ from the control feed except for the incorporation of the adjuvant according to the invention comprising a *Scutellaria baicalensis* extract.

The weight of the piglets was identical in both groups at birth.

Table 3 below presents the effects of a *Scutellaria baicalensis* extract on the milk production of sows as assessed by the growth of the nursed piglets (ADWG—Average Daily Weight Gain in grams of the nursed piglets). The weight at weaning and the ADWG are significantly higher in the piglets suckled by a sow that consumed feed supplemented with *Scutellaria baicalensis*.

TABLE 3

Average weight of piglets according to the feed of the sow

| | Average weight of the piglets at birth (kg) | Weight at weaning (kg) | ADWG (g/d) |
|---|---|---|---|
| Control | 1.33 | 5.68 | 235 |
| *Scutellaria baïcalensis* | 1.32 | 6.04 | 264 |
| Comparison of average-significance | ns | <0.001 | <0.001 |

The weight of the piglets reveals a higher growth in piglets whose mothers consumed feed comprising a *Scutellaria baicalensis* extract. This shows that the milk production of sows is stimulated by the *Scutellaria baicalensis* extract.

Test 3: Study of the Effect of the Administration of a Feed Comprising the Adjuvant with the *Scutellaria baicalensis* Extract on a Solid Vehicle on the Feed Intake of Laying Hens Subject to Thermal Stress Protocol:

72 Isabrown laying hens thirty weeks old at the beginning of the test were divided into three groups of twelve cages each containing two hens. The test was carried out until the hens were 38 weeks old.

Group 1 received the control feed. The characteristics are provided in table 4.

Group 2, also called the OTC group, received the control feed supplemented with an antibiotic, 400 ppm of oxytetracycline.

Group 3, also called the SCU group, received the control feed supplemented with an extract from the root of *Scutellaria baicalensis* providing 6 mg of baicalin/kg of feed.

TABLE 4 formula of the basic feed distributed

| Raw materials | % |
|---|---|
| WHEAT | 30.00 |
| MAIZE | 36.62 |
| SOY meal | 21.40 |
| SOY oil | 0.80 |
| BICARBONATE of sodium | 0.12 |
| BICALCIUM PHOSPHATE | 1.26 |
| CARBONATE | 7.54 |
| SALT | 0.28 |
| METHIONINE 15/WHEAT 85 | 0.98 |
| Mineral and vitamin supplement | 1 |

After three weeks of distribution of the experimental feed, the hens were subject to a variation in temperature. The temperature of the environment increased from 22° C. (thermal comfort) to 35° C. for 5 days. Food intake, number of eggs laid and average weight of the eggs were recorded every week and every day during the week of the high temperature as well as during the following week.

The test was divided into three phases: pre-heat increase phase, thermal stress phase and post-high temperature stress phase.

Results:

The consumption during the pre-thermal increase phase is identical in all of the groups. During the thermal stress phase, the daily feed intake per hen was 50.9 g, 53.5 g and 59.7 g for the control, OTC and SCU groups respectively. The intake was significantly higher in the SCU group ($p<0.05$). The group 3, SCU laying hens increased their feed intake by 17% during the thermal stress phase. The egg-laying rate over the 2 weeks including the thermal stress phase and the following week are 85.2, 88.5 and 87.2% for the hens receiving the control feed, the feed supplemented with the antibiotic and the *Scutellaria baicalensis* extract, respectively.

Test 4: Study of the Effect of the Administration of a Feed Comprising an Adjuvant Consisting of an Extract of *Scutellaria baicalensis* on a Solid Vehicle on the Growth of Chickens Subject to a High Temperature 160 Ross PM3 yellow chickens were divided into four groups of 20 cages, each with two chickens. Group 1 was the control group. The composition of the feed that the group 1 chickens received is provided in table 5. Group 2 received the control feed supplemented with an adjuvant according to the invention comprising an extract of *Scutellaria baicalensis* at 3 mg of baicalin/kg of feed. Group 3 received the same feed with 6 mg of baicalin/kg and Group 4, 9 mg/kg of feed. In view of the intake, it was possible to calculate the average dose of baicalin consumed per kg of raw weight (table 6, FIG. 3). The *Scutellaria baicalensis* extract was provided by an adjuvant containing 0.5% extract and 99.5% wheat instead of the wheat in the formula.

TABLE 5

Composition of the basic feed distributed

| INGREDIENT | % |
|---|---|
| WHEAT | 30.00 |
| MAIZE | 34.25 |
| SOY grains | 4.20 |
| Soy meal | 25.70 |
| SOY oil | 1.50 |
| BICARBONATE of SODIUM | 0.21 |
| BICALCIUM PHOSPHATE | 1.43 |
| CARBONATE | 0.62 |
| SALT | 0.20 |
| METHIONINE 15/WHEAT 85 | 1.07 |
| L-LYSINE 20/WHEAT 75 | 0.42 |
| Vitamin and trace minerals PREMIX | 0.40 |

From day 25 to day 30, the chickens were subjected to an artificial increase in the temperature from 22° C. to 36° C. in order to induce a thermal stress.

The chickens were weighed before and after the thermal stress phase and their feed intake was measured (day 24 and day 30). The test continued until day 30.

Results:

Table 6 sums up the results obtained in the four groups of chickens during the thermal stress phase (day 24 to day 30).

TABLE 6

Weight of the chickens according to their feed

| Group | Dose (mg/kg of live weight/day) | Initial weight before the thermal stress phase (g) | Final weight after the thermal stress phase (g) | ADWG (g/d) | ADI (g/d) | TCI |
|---|---|---|---|---|---|---|
| Control | 0 | 1290 | 1786 | 82.6 | 152.2 | 1.94 |
| Baicalin | 0.3 | 1305 | 1852 | 91.1 | 162.3 | 1.80 |
| Baicalin | 0.6 | 1257 | 1837 | 96.6 | 168.5 | 1.74 |
| Baicalin | 0.9 | 1288 | 1804 | 86.0 | 157.0 | 1.94 |
| Comparison of average - significance (initial weight as a covariable) | | ns | <0.01 | 0.05 | <0.01 | 0.06 |

ADWG, average daily weight gain
ADI, average daily intake
TCI, technical consumption index Before the period of stress resulting from a high temperature in the buildings, the growth of the birds receiving the two feeds was identical (the weight at day 24 did not differ in the groups). The average daily intake (ADI) in the group receiving the feed comprising an extract of *Scutellaria baicalensis* at the rate of 0.6 mg/kg of live weight and per day was higher by 10.7% and the average daily weight gain (ADWG) was 17% higher during the thermal stress phase than in the control group. This led to a better growth of the treated chickens than the chickens in the control group. The 0.6 mg dose of baicalin per kg of live weight and per day is the dose providing the most interesting effects (FIG. 3).

Test 5: Study of the Effect of the Administration of a Feed Comprising the Adjuvant with the Extract of *Scutellaria baicalensis* on a Solid Vehicle on the Improvement in the State of Health and Resistance to Disease of Piglets Subject to a Stress The piglets were 42 days old at the beginning of the test. Three groups were formed: a control group, a group receiving the same feed supplemented with 100 ppm of an antibiotic (tylosine) and finally the last group receiving a feed supplemented with 100 ppm of an extract of *Scutellaria baicalensis*, that is 30 ppm of baicalin per kg of feed. The diseases were noted as were the curative treatments used in each groups. The results are provided in table 7.

TABLE 7

Pathological episodes in weaned piglets according to their feed.

| | Control | Tylosine antibiotic (100 ppm in the feed) | Extract of *Scutellaria baicalensis* (100 ppm in the feed) | P (Chi2) |
|---|---|---|---|---|
| Pigs in test | 19 | 25 | 20 | |
| Number of deaths | 0 | 0 | 0 | |
| Withdrawn from test | 0 | 1 | 0 | |
| Mortality + elimination (%) | 0.0 | 4.0 | 0 | |
| Number of treatments | 15 | 14 | 5 | <0.05 |
| % treatments | 78.9 | 56.0 | 25 | |
| Watery diarrhoea | 7 | 4 | 3 | |
| Lean | 0 | 2 | 0 | |
| Lame | 0 | 0 | 0 | |
| Cough | 8 | 7 | 2 | |
| Nervous symptoms | 0 | 1 | 0 | |

TABLE 7-continued

Pathological episodes in weaned piglets according to their feed.

| | Control | Tylosine antibiotic (100 ppm in the feed) | Extract of *Scutellaria baicalensis* (100 ppm in the feed) | P (Chi2) |
|---|---|---|---|---|
| Number of pigs treated | 13 | 13 | 5 | <0.05 |
| % Pigs treated | 68.4 | 52 | 25 | |
| % Pigs not treated | 31.6 | 48 | 75 | |
| Pigs treated per cause | | | | |
| Watery diarrhoea | 7 | 4 | 3 | |
| Lean | 0 | 2 | 0 | |
| Lame | 0 | 0 | 0 | |
| Cough | 8 | 7 | 2 | |
| Nervous symptoms | 0 | 1 | 0 | |

A significant reduction in disease is observed in the group receiving the adjuvant in the feed comprising according to the invention an extract of *Scutellaria baicalensis* and a reduction in the number of curative treatments is also observed. The typology of the symptoms noted shows a non-specific general improvement in the state of health due to an improvement in the digestive problems and the respiratory problems.

The invention claimed is:

1. A method of increasing the rate of lactation in a lactating cow or sow, the method comprising providing a feed comprising baicalin and/or baicalein and administering the feed to the lactating cow or sow, wherein the feed is administered at a rate that results in delivery to the farm animal of from 0.1 to 10 mg of baicalin and/or baicalein per kg of live weight per day, and wherein administering the feed to the lactating cow or sow increases the rate of lactation in the lactating cow or sow in comparison to administering comparable feed that does not comprise baicalin and/or baicalein.

2. The method of claim 1, wherein the feed is administered at a rate that results in delivery to the lactating cow or sow of from 0.1 to 5 mg of baicalin and/or baicalein per kg of live weight per day.

3. The method of claim 2, wherein the feed is administered at a rate that results in delivery to the farm animal of from 0.1 to 2 mg of baicalin and/or baicalein per kg of live weight per day.

4. The method of claim 1, wherein the farm animal is undergoing discomfort or stress.

* * * * *